(12) United States Patent
Torabinejad et al.

(10) Patent No.: US 7,238,342 B2
(45) Date of Patent: Jul. 3, 2007

(54) IRRIGATION SOLUTION AND METHODS FOR USE

(75) Inventors: Mahmoud Torabinejad, Loma Linda, CA (US); William B. Johnson, Tulsa, OK (US)

(73) Assignee: Dentsply International, York, PA (US)

( * ) Notice: Subject to any disclaimer, the term of this patent is extended or adjusted under 35 U.S.C. 154(b) by 435 days.

(21) Appl. No.: 10/348,298

(22) Filed: Jan. 21, 2003

(65) Prior Publication Data

US 2003/0235804 A1 Dec. 25, 2003

Related U.S. Application Data

(63) Continuation-in-part of application No. 10/055,075, filed on Jan. 23, 2002, now abandoned.

(51) Int. Cl.
*A61K 31/65* (2006.01)
*A61C 17/00* (2006.01)
*A61K 8/00* (2006.01)

(52) U.S. Cl. .................. 424/49; 433/216; 433/224; 433/228.1; 514/154; 514/901; 424/53

(58) Field of Classification Search .............. 424/49; 433/216, 224
See application file for complete search history.

(56) References Cited

U.S. PATENT DOCUMENTS 3,846,548 A  11/1974  Akazawa et al. ........... 424/227

OTHER PUBLICATIONS

Aktener, B.O. et al., "Smear Layer removal with different concentrations of EDTA-Ethylenediamine mixtures", *J. Endodon.*, 1993, 19, 228-231.
Barkhordar, R.A. et al., "Effect of doxyxyxline on the apical seal of retrograde filling materials", *Cal. Dent. Assn. J.*, 1998, 26, 841-844.
Barkhordar, R.A. et al., "Removal of intracanal smear by doxycycline in vitro", *Oral Surg. Oral Med. Oral Path.*, 1997, 84, 420-423.
Baumgartner, J.C., et al., "A scanning electron microscopic evaluation of root canal debridement using saline, sodium hypochlorite, and citric acid", *J. Endodon.*, 1984, 10, 525-531.
Berg, M.S. et al., "A comparison of five irrigating solutions: A scanning electron microscopic study", *J. Endodon.*, 1986, 12, 192-197.
Berry, B.A., et al., "Dentin surface treatments for the removal of the smear layer: an SEM study", *J. A.D.A.*, 1987, 115, 65-67.
Bitter, N.C., "A 25% tannic acid solution as a root canal irrigant cleanser: A scanning electron microscope study", *Oral Surg. Oral Med. Oral Path.*, 1989, 67, 333-337.
Bystrom, A., et al., "The antibacterial effect of camphorated paramonochlorophenol, camphorated phenol and calcium hydroxide in the treatment of infected root canals" *Endod. Dent. Tramatol.*, 1985, 1, 170-175.
Calt, S., et al., "Smear layer removal by EGTA", *J. Endodon.*, 2000, 26, 459-461.
Cengiz, T. et al., "The effect of dentinal tubule orientation on the removal of smear layer by root canal irrigants. A scanning electron microscopic study", *Int'l Endodon J.*, 1990, 23, 163-171.
Chong, B.S., et al., "The role of intracanal medication in root canal treatment", *Int'l Endodon. J.*, 1992, 25, 97-106.
Jeong, S., et al., "Effects of tetracycline-containing gel and a mixture of tetracycline and citric acid-containing gel on non-surgical peridontal theraphy", *J. Periodontol.*, 1994, 65, 840-847.
Karagoz-Kucukay, I. et al., "The apical leakage study in the presence and absence of the smear layer", *Int'l Endod. J.*, 1994, 27, 87-93.
Kaufman, A.Y., "The use of dequalinium acetate as a disinfectant and chemotherapeutic agent in endodontics", *Oral Surg.*, 1981, 51, 434-441.
Kaufman, A.Y., et al., "New chemotherapeutic agent for root canal treatment", *Oral Surg.*, 1978, 46, 283-295.
Kaufman, A.Y. et al., "Comparative study of the configuration and the cleanliness level of root canals prepared with the aid of sodium hypochlorite and bis-dequalinium-acetate solutions", *Oral Surg.*, 1986, 62, 191-196.
Loel, D.A., "Use of acid cleanser in endodontic theraphy", *J.A.D.A.*, 1975, 90, 148-151.
McComb, D., et al., "A preliminary scanning electron microscopic study of root canals after endodontic procedures", *J. Endodon.*, 1975, 1, 238-242.
Morgan, L.A., et al., "Demineralization of resected root-ends with methylene blue dye", *Oral Surg. Oral Med. Oral Path.*, 1997, 84, 74-78.
O'Connell, M.S. et al., "A comparative study of smear layer removal using different salts of EDTA", *J. Endodon.*, 2000, 26, 739-743.
Pallares, A., et al., "The adaptationof mechanically softened gutta-percha to the canal walls in the presence or absence of smear layer: a scanning electron microscopic study", *Endodon, J.*, 1995, 28, 266-269.
Sabbak, S.A., et al., "A scanning electron microscopic study of tooth surface changes induced by tannic acid", *J. Prosthet. Dent.*, 1998, 79, 169-174.
Saunders, W.P. et al., "Influence of smear layer on the coronal leakage of thermafil and laterally condensed gutta-percha root fillings with a glass ionomer sealer", *J. Endodon.*, 1994, 20, 155-158.
Takeda, F.H. et al., "A comparative study of the removal of smear layer by three endodontic irrigants and two types of laser", *Int'l Endodon. J.*, 1999, 32, 32-39.
Tam, A., et al., "An evaluation of the effectiveness of two canal lubricants in removing smear layer", *Compendium Cont. Ed. Dent.*, 2000, 21, 967-972.
Tidmarsh, B., "Acid-cleansed and resin-sealed root canals", *J. Endodon.*, 1978, 4, 117-121.
Wayman, B.E. et al., "citric and lactic acids as root canal irrigants in vitro", *J. Endodon.*, 1979, 5, 258-265.
Yamada, R.S. et al., "A scanning electron electron microscopic comparasion of a high volume final flush with several irrigating solutions: part 3", *J. Endodon.*, 1987, 13, 137-142.

*Primary Examiner*—Ardin H. Marschel
*Assistant Examiner*—Donna Jagoe
(74) *Attorney, Agent, or Firm*—Woodcock Washburn LLP

(57) ABSTRACT

Methods and solutions are provided for removal of the smear layer on prepared tooth and bone surfaces, especially in endodontic environments.

4 Claims, No Drawings

IRRIGATION SOLUTION AND METHODS FOR USE

This application is a Continuation in Part of U.S. application Ser. No. 10/055,075, filed Jan. 23, 2002 now abandoned, which is herein incorporated by reference in its entirety.

The present invention relates to methods and solutions for removing undesirable substances from tooth surfaces during dental procedures. The invention removes buildup of debris and bacteria formed during preparation of tooth surfaces during procedures such as root canal treatment, restoration, dental reconstruction, periodontal procedures, and the like, and is also suitable for preparation of bone for reconstruction or restoration.

As a consequence of pathological changes in the dental pulp, the root canal system acquires the capacity to harbor several species of bacteria, their toxins and their by-products. The microorganisms present in infected root canals are predominantly gram-negative anaerobes that are seeded into the root canals from direct pulp exposures (caries or traumatic injuries) or coronal microleakage. The morphology of root canals is very complex and mechanically prepared root canals contain areas that cannot be reached by endodontic instruments. The microorganisms present in the root canal not only invade the anatomic irregularities of the root canal system, but also invade the dentinal tubules.

In the root, dentinal tubules extend from the intermediate dentin just inside the cementum-dentin junction to the pulp-predentin junction. Tubules are approximately 1 µm in diameter near the cementum-dentin junction and approximately 2.5 µm near the pulp-predentin junction. The number of dentinal tubules per square millimeter varies from 8,000 to 57,000. At the periphery of the root at the cemento-enamel junction, the number has been estimated to be approximately 15,000 per square millimeter.

Many studies have shown that currently used methods of cleaning and shaping produce a smear layer that covers root canal walls. The smear layer is produced as a result of instrumentation and its content is forced into the dentinal tubules to varying distances. Moodnik, R. M., Dorn, S. O., Feldman, M. J., Levey, M., and Borden, B. G., J. Endodon., 1976, 2, 261-266; Cengiz, T., Aktener, B. O., and Piskin, B., Int'l. Endodon. J., 1990, 23, 163-171. Cengiz, et al. suggested that the penetration of smear material into the dentinal tubules is probably caused by capillary action generated between the dentinal tubules and the smear material.

In 1975, McComb and Smith described the smear layer in endodontics. McComb, D., and Smith, D. C., J. Endodon., 1975, 1, 238-242. It was later characterized as consisting of a superficial layer on the surface of the canal wall that averages between 1-2 µm in thickness, and a deeper layer packed into the dentinal tubules to a depth of up to 40 µm. Cameron, J. A., J. Endodon., 1983, 9, 289-292; Mader, C. L., Baumgartner, J. C., and Peters, D. D., J. Endodon., 1984, 10, 477-483. The smear layer consists of organic and inorganic substances that include fragments of odontoblastic processes, microorganisms and necrotic materials. A number of studies have shown that presence of smear layer can prevent penetration of root canal medications and sealers into the dental tubules. In addition, they have shown that removal of the smear layer results in better adaptation between root canal filling materials and the dentinal walls.

Bacteria present in the infected root canals usually invade the dentinal tubules and can re-infect the root canals if they remain viable after root canal therapy. Viable bacteria has been reported in dentinal tubules of infected teeth at approximately half the distance between the root canal walls and the cemento-dentinal junction. Endotoxins have been found within the dentinal walls of infected root canals as well. Concern has been evidenced regarding the fate of these bacteria, especially whether they may find nutrients for growth and reproduction.

Complete eradication of bacteria present in the canals and dentinal tubules, sealing root canals in three dimensions and prevention of recontamination of sealed root canals are the ideal goals for endodontic therapy. Because of the complexity of root canal systems, and the inability of instruments to contact all surfaces of the root canals, it is impossible to create a sterile space in all teeth with infected root canals. Bystrom, A., and Sundqvist, G., Scand, J. Dent. Res., 1981, 89, 321-328; Bystrom, A., Claesson, R., and Sundqvist, G., Endod. Dent. Traumatol., 1985, 1, 170-175. In fact, residual bacteria in an instrumented and unfilled canal can multiply to their original numbers within 2-4 days. To prevent repopulation of the root canals with residual bacteria, the use of intracanal medications and completion of treatment of infected root canals in more than one visit has been recommended. Bystrom, A., Claesson, R., and Sundqvist, G., Endod. Dent. Traumatol., 1985, 1, 170-175; Chong, B. S., and Pitt Ford, T. R., Int'l. Endodon. J., 1992, 25, 97-106.

Intracanal medications have traditionally been considered important to success of root canal therapy. In fact, it has been a common assumption that success, both short- and long-term, depends on the chemicals placed in the canal between appointments. However, there is no firm scientific evidence for usefulness of medications such as camphorated monochlorophenol (CMCP), formocresol, cresatin, or calcium hydroxide ($Ca(OH)_2$), which have been used as intracanal medications. The intracanal medications have been proposed for, inter alia, antimicrobial use in the pulp and periapex, neutralization of canal remnants to render them inert, and control or prevention of post-treatment pain.

A study of the presence and influence of bacteria on the long-term success of root canal therapy showed that about 40% of root canals are infected after instrumentation. Sjogren, U., Figdor, D., Persson, S., and Sundqvist, G., Int'l; Endodon. J., 1997, 30, 297-306. In addition, instrumented canals without application of an intracanal medication with $Ca(OH)_2$ failed significantly more frequently than those which were medicated for one week with $Ca(OH)_2$ (68% vs. 94%). The results of this study corroborate a 1987 study showing improved clinical success rates following effective disinfection of root canals. Bystrom, A., Happonen, R., Sjogren, U., and Sundqvist, G., Endod. Dent. Traumatol., 1987, 3, 58-63.

According to a number of authorities, presence of smear layer can inhibit penetration of anti-microbial agents such as intra-canal irrigants and medications into the dentinal tubules. Haapasalo, M., and rstavik, D., J. Dent. Res., 1987, 66, 1375-1379; Czonstkowsky, M., Wilson, E., and Holstein, F., Dental Clinics of N. Am., 1990, 34, 13-24. Several investigators have reported better adhesion of obturation materials to the canal walls after removal of the smear layer. Goldberg, F., and Abramovich, A., J. Endodon., 1977, 3, 101-105; White, R. R., Goldman, M., and Lin, P. S., J. Endodon., 1984, 10, 558-562. Several studies have also reported poor or no penetration of sealer in tubules with an intact smear layer. These studies have shown improved penetration following removal of the smear layer with sealers such as Tubliseal (penetration to 15 µm); AH26 (penetration from 10-60 µm); and Sealpex, Roth's 811, and CRCS (all with penetration from 35-80 µm). Gutierrez, J. H., Herrera, V. R., Berg, E. H., Villena, F., and Jofre, A., Oral Surg. Oral Med. Oral Path., 1990. 70, 96-108; Pallares, A., and Faus, V., Int'l. Endodon. J., 1995, 28, 266-269; Kouvas, V., Liolios, E., Vassiliadis, L., Parissis-Messismeris, S., and Boutsioukis, A., Endod. Dent. Traumatol., 1998, 14, 191-195.

Additionally, the presence or absence of the smear layer is believed to play an important role in the adhesive strength of a sealer to the dentinal walls. One study found a significant increase in adhesive strength of AH26 sealer when the smear layer was removed. Gettleman, B. H., Messer, H. H., and ElDeeb, M. E., J. Endodon., 1991, 17, 15-20. These findings correlate with the results of another study demonstrating an increase in resistance to microleakage of AH26 when the smear layer was removed. Economides, N., Liolios, E., Kolokuris, I., and Beltes, P., J. Endodon., 1999, 25, 123-125.

Contrary to these findings, some studies have found that the presence or absence of the smear layer has no significant effect on apical leakage. Evans, J. T. and Simon, J. H. S., J. Endodon., 1986, 12, 101-107. Kennedy, W. A., Walker, W. A., and Gough, R. W., J. Endodon., 1986, 12, 21-27; Economides, N., Liolios, E., Kolokuris, I., and Beltes, P., J. Endodon., 1999, 25, 123-125; Timpawat, S., and Sripanaratanakul, S., J. Endodon., 1998, 24, 343-345.

It has been shown that removal of smear layer before sealing of the root canal system allows better adaptation between the obturation materials and the root canal walls. Yamada, R. S., Armas, A., Goldman, M., and Lin, P. S., J. Endodon., 1983, 9, 137-142; Czonstkowsky, M., Wilson, E., and Holstein, F., Dental Clinics of N. Am., 1990, 34, 13-24. One study examined the adaptation of a mechanically softened gutta percha to the dentinal walls and reported that removal of the smear layer resulted in entry of gutta percha into the dentinal tubules. Pallares, A., and Faus, V., Int'l. Endodon. J., 1995, 28, 266-269. These authors reported no gutta percha penetration into the dentinal tubules in canals with intact smear layer. Another study reported that when Thermafil, Ultrafill and cold lateral condensation techniques were used as obturation methods, all techniques showed significant resistance to microleakage with the smear layer removed. Gencoglu, N., Samani, S., and Gunday, M., J. Endodon., 1993, 19, 558-562. Vertical condensation of gutta percha, Thermafil, and lateral compaction techniques with Ultrafill have also been reported to reduce microleakage with the smear layer removed. Taylor, J. K., Jeansonne, B. G., and Lemon, R. R., J. Endodon., 1997, 23, 508-512; Karagoz-Kucukay, I., and Bayirli, G., Int'l. Endod. J., 1994, 27, 87-93. In contrast to these findings, some studies have reported that removal of smear layer had no significant effect on microleakage of canals filled with laterally condensed gutta percha or Thermafil and System B (warm vertical) obturation techniques. Saunders, W. P., and Saunders, E. M., J. Endodon., 1994, 20, 155-158; Kytridou, V., Gutmann, J. L., and Nunn, M. H., Int'l. Endodon. J., 1999, 32, 464-474. Even if the smear layer can not be fully removed, one of skill in the art will recognize that it is desirable to remove as much of the smear layer as possible, while sterilizing the portion that remains, prior to proceeding with filling, reconstruction, restoration, or final treatment.

The components of the smear layer are very small particles with a large surface/mass ratio, which makes them very soluble in acids. Because of this characteristic, certain acids have been used in an attempt to remove the smear layer. Different formulations of ethylenediamine tetraacetic acid (EDTA) have been used to remove the smear layer from the surface of instrumented root canals, including REDTA (Roth EDTA). McComb, D., and Smith, D. C., J. Endodon., 1975, 1, 238-242. Some investigators, however, have questioned the effectiveness of REDTA by showing that when used alone, REDTA removes the inorganic portion of the smear layer but leaves an organic layer intact in the tubules. Goldman, M., Goldman, L. B., Cavaleri, R., Bogis, J., and Lin, P. S., J. Endodon., 1982, 8, 487-492. Sodium hypochlorite (NaOCl) has been shown to be very effective against this organic layer. When used alone, NaOCl can dissolve pulpal remnants, as well as predentin, but is ineffective in removing the smear layer. The alternating use of EDTA and NaOCl, however, has been reported to be an effective method to remove the smear layer. Goldman, M., Goldman, L. B., Cavaleri, R., Bogis, J., and Lin, P. S., J. Endodon., 1982, 8, 487-492; Yamada, R. S., Armas, A., Goldman, M., and Lin, P. S., J. Endodon., 1983, 9, 137-142; Baumgartner, J. C., and Mader, C. L., J. Endodon., 1987, 13, 147-157. One study recommends the use of NaOCl during instrumentation, along with an EDTA rinse followed by a final flush with NaOCl. Baumgartner, J. C., and Mader, C. L., J. Endodon., 1987, 13, 147-157. Another study compared the ability of various salts of EDTA to remove the smear layer and concluded that all salts of EDTA were capable of removing the smear layer from the coronal two thirds of root canals. In addition, the same study reported that tetrasodium salt, pH adjusted with HCl, is less expensive and just as effective as the more commonly used disodium EDTA. O'Connell, M. S., Morgan, L. A., Beeler, W. J., and Baumgartner, J. C., J. Endodon., 2000, 26, 739-743.

In 1993, a solution of EDTA and ethylenediamine was developed to work in a dual action. Aktener, B. O., and Bilkay, U., J. Endodon., 1993, 19, 228-231. The goal was to see if a single irrigating solution can be developed to remove the inorganic as well as the organic components of the smear. Many patent tubules were found, but more research was deemed necessary to determine the efficacy of this combination. Other studies have added a quaternary ammonium bromide to EDTA to reduce its surface tension. Goldberg, F., and Abramovich, A., J. Endodon., 1977, 3, 101-105; Ciucchi, B., Khettabi, M., and Holz, J., Int'l. Endod. J., 1989, 22, 21-28. This addition increased the wetting effect on the canal wall and permitted deeper penetration of the solution into irregularities. EDTAC, as it is named, was shown to be very effective in smear layer removal, reaching its peak effect at 15 minutes and increasing the diameter of the opened dentinal tubules. Goldberg, F., and Spielberg, C., Oral. Surg., 1982, 53, 74-77. Another study reported effective removal of the smear layer when using a solution of EDTA, carbamide peroxide, and propylene glycol. Tam, A., and Yu, D. C., Compendium Cont. Ed. Dent., 2000, 21, 967-972. Recently, ethylene glycol-bis (b-aminoethyl ether —NNNN-tetraacetic acid), EGTA, was reported to be somewhat effective in removing the smear layer without inducing erosion commonly caused by EDTA. Calt, S., and Serper, A., J. Endodon., 2000, 26, 459-461.

The quantity of smear layer removed by an acid is directly related to the concentration of the acid (pH) and the time of exposure. Morgan, L. A., and Baumgartner, J. C., Oral Surg. Oral Med. Oral Path., 1997, 84, 74-78. Several studies used a 50% citric acid solution to treat canal walls after instrumentation and found better penetration of rosin sealer into the walls and improved adaptation of gutta percha when compared to untreated canals. Loel, D., J. A. D. A., 1975, 90, 148-151; Tidmarsh, B., J. Endodon., 1978, 4, 117-121; Baumgartner, J. C., Brown, C. M., Mader, C. L., Peters, D. D., and Shulman, J. D., J. Endodon., 1984, 10, 525-531. When citric acid was used as the sole agent for removal of smear layer, solutions at concentrations below 50% were ineffective. Yamada, R. S., Armas, A., Goldman, M., and Lin, P. S., J. Endodon., 1983, 9, 137-142; Takeda, F. H., Harashima, T., Kimura, Y., and Matsumoto, K., Int'l. Endodon. J., 1999, 32, 32-39. Lactic acid at 50% concentration is less effective than 50% citric acid for removal of smear layer. Wayman, B. E., Kopp, W. M., Pinero, G. J., and Lazzari, E. P., J. Endodon., 1979, 5, 258-265. This could possibly be attributed to the viscosity of lactic acid. Additionally, alternating use of 10% citric acid and 2.5% NaOCl has also been reported to be a very effective method for removing the smear layer. Wayman, B. E., Kopp, W. M., Pinero, G. J., and Lazzari, E. P., J. Endodon., 1979, 5, 258-265.

In 1989, one study reported that 25% tannic acid was effective in removing the smear layer, but another study refuted these findings and explained that tannic acid increased the cross-linking of exposed collagen within the smear layer and within the matrix of the underlying dentin, thus increasing organic cohesion to the tubules. Bitter, N. C., Oral Surg. Oral Med. Oral Path., 1989, 67, 333-337; Sabbak, S. A., and Hassanin, M. B., J. Prosthet. Dent., 1998, 79, 169-174.

Polyacrylic acid (Durelon liquid and Fuji II liquid) at 40% has been reported to be very effective for removal of smear layer. Berry, B. A., von der Lehr, W. N., and Herrin, B. K., J. A.D.A., 1987, 115, 65-67. Because of its potency, however, it is recommended that application of Polyacrylic acid should not exceed 30 seconds.

Derivatives of oxine (8-hydroxy-quinoline) have been known to possess antiseptic qualities as early as 1895. Dequalinium compounds, which belong to this group, have been widely used in medicine against infections of bacteria, molds and fungi. Bis-dequalinium-acetate (BDA) has been shown to remove the smear layer throughout the canal, even in the apical third. Kaufman, A. Y., Binderman, I., Tal, M., Gedalia, I., and Peretz, G., Oral Surg., 1978, 46, 283-295; Kaufman, A. Y., Oral Surg., 1981, 51, 434-441. BDA is well tolerated by the tissues within the periodontium and has a low surface tension that allows penetration into spaces that instruments cannot reach. BDA is also considered less toxic than NaOCl and can be used interoperatively as a root canal dressing. One study compared Salvizol (a commercial brand of 0.5% BDA) with 5.25% NaOCl and found both comparable in their ability to remove organic debris, but only Salvizol was able to open dentinal tubules. Kaufman, A. Y., and Greenberg, I., Oral Surg., 1986, 62, 191-196. Another study reported Salvizol to be less effective at opening dentinal tubules compared to REDTA. Berg, M. S., Jacobsen, E. L., BeGole, E. A., and Remeikis, N. A., J. Endodon., 1986, 12, 192-197.

The effects of the tetracycline family of antibiotics on removal of smear layer have also been studied to a degree. These materials have been used to demineralize dentin surfaces, uncover and widen the orifices of dentinal tubules and expose the dentin collagen matrix. These effects provide a matrix that stimulates fibroblast attachment and growth. Studies have shown that doxycyline HCl (100 mg/ml) is an effective material to remove the smear layer from the surfaces of instrumented canals and those prepared for root-end filling materials. Barkhordar, R. A., Watanbe, L. G., Marshall, G. W., and Hussain, M. Z., Oral Surg. Oral Med. Oral Path., 1997, 84, 420-423; Barkhordar, R. A., and Russel, T., Cal. Dent. Assn. J., 1998, 26, 841-844; Haznedaroglu, F. and Ersev, H., J. Endodon., 2001, 27, 738-740. These studies speculate that a reservoir of active antibacterial agent might be created since doxycycline readily attaches to dentin and can be readily released later. Another study has reported increased demineralization effect when a 5% tetracycline/33% citric acid gel was used to treat teeth with moderate periodontal disease. Jeong, S., Han, S., Lee, S., and Magnusson, I., J. Periodontol., 1994, 65, 840-847.

Apart from chemical solutions, mechanical methods, including ultrasonic instrumentation, have been widely reported to be effective in removing the smear layer from prepared tooth surfaces. Laser removal of the smear layer has been shown to be successful as well for vaporizing tissues in the main canal, removing the smear layer, and eliminating residual tissue in the apical portion of root canals. Since laser beams travel in straight lines, however, the use of lasers in curved canals is limited.

Smear layers are also formed when tooth material is removed preparatory to restoration or other dental work, as it is for root canal situations. Moreover, in the restoration of bone, such as in orthopaedic restorations, debris layers similar in many respects to endodontic smear layers are also formed. It is now believed that their removal would be highly desirable as well.

Accordingly, it is believed to be highly desirable to remove the smear layer from a prepared root canal space prior to filling the canal. However, removal of smear layer materials is very difficult to accomplish. Moreover, there are no present methods likely to effect substantially complete removal of smear layers. Prior attempts have used a number of chemical species to remove the smear layer and sterilize the root surface(s), but with indifferent results. The removal of smear layer materials with a unitary solution to yield effective, convenient, and rapid smear layer removal is desired. All of this must be accomplished without interfering with the essential purpose of root canal preparation or with the eventual restoration of the space. Removal of smear layers from tooth restoration sites, periodontal loci, and other prepared locations for dental and periodontic work is a further object. Indeed, it is also believed to be desirable to remove smear layers from orthopaedic and bone restoration sites within or without the oral cavity as well.

SUMMARY OF THE INVENTION

The present invention provides methods for removing smear layers from and sterilizing endodontic excavations and other prepared tooth surfaces by irrigating with a mixture comprising disinfectant, detergent, and acid, especially organic acid. In a further aspect, the present invention relates to solutions for irrigating prepared tooth surfaces to remove smear layers as well as to restorations employing the method. Application to bone excavations is also contemplated.

It has now been discovered that a solution combining disinfectant, detergent, and acid is highly effective for removing the smear layer on prepared dental surfaces and dentinal tubules. Such solutions are useful in a multitude of dental applications, including, but not limited to, root canal therapy; preparation of cavities; cosmetic and reconstructive dentistry such as caps, crowns, bridges, veneers, and the like; other endodontic procedures; periodontic procedures; and bone preparation or restoration. Such solutions are also useful in improving orthopaedic restoration sites as well.

The term "smear layer" as used herein, is well known to persons skilled in the art of dentistry and refers to the complex accumulation of organic and inorganic debris resulting from the mechanical preparation of a tooth surface. The smear layer comprises cutting debris, tooth particles, microorganisms, necrotic material, and other substances resulting from preparation, and typically includes a superficial layer on the surface of a prepared tooth along with a layer or layers that are packed into the adjacent dentinal tubules at varying depths up to about 40 μm. In the context of orthopaedics, "smear layer" refers to similar layers in prepared bone sites.

The term "disinfectant", as used herein, refers collectively to compositions that are able to suppress or eliminate bacterial or other microorganisms found in endodontic or periodontic sites. The term "disinfectant" includes antibiotics as that term is understood in pharmaceutical science.

The components of this invention comprise disinfectant, detergent, and acid. In a preferred embodiment, the disinfectant is an antibiotic. It will be apparent to one skilled in the art that the antibiotic should be stable in the acidic solutions of which it forms a part, should be compatible with the other components of the solution, and should retain its effectiveness for at least the time of preparation of the solution and its application and residence time on or in the prepared tooth or bone surface. Examples of such antibiotics include, but are not limited to, ansamycins, including rifamycins; cephalosporin; macrolides such as clarithromycin, josamycin, and oleandomycin; most polypeptides, such as bacitracin, capreomycin, enduracidin, enviomycin, gramicidin, mikamycin, ristocetin, thiostrepton, tyrocidine, viomycin, and virginiamycin; all tetracycline compounds, such as apicycline, chlortetracycline, clomocycline, demeclocycline, doxycycline, guamecycline, lymecycline, mecleocycline, methacycline, minocycline, oxytetracycline, penimepicycline, pipacycline, rolitetracycline, sancycline, mupirocin, and tetracycline-HCl; and tuberin. Most quinolones such as ciprofloxacin, gatifloxacin, and moxifloxacin are not preferred, as they are weak bases and have decreased effect in acidic solutions. Additionally, most B-lactam antibiotics, particularly penicillins, are also not preferred, as they are generally unstable in acidic solutions. Exceptions, however, are amoxycillin, an acid-stable member of the penicillin family, and similar compounds.

Tetracyclines are broad-spectrum antibiotics that are effective against a wide range of microorganisms. They include tetracycline-HCl, minocycline, and doxycycline. Tetracyclines are bacteriostatic in nature and are generally more effective against gram-positive bacteria compared to gram-negative bacteria. A reference to tetracycline shall be taken to include all members of the tetracycline family. A number of studies have shown that tetracyclines significantly enhance healing after surgical periodontic therapy. Members of the family of tetracyclines are preferred for use herein. Tetracyclines are preferred for a number of reasons. One reason they are preferred is because they have many unique properties along with their antimicrobial effect. For example, tetracycline-HCl has a low pH in concentrated solution and thus can act as a calcium chelator, and cause enamel and root surface demineralization. Tetracycline-HCl's surface demineralization of dentin is comparable to that seen using citric acid. In addition, it has been shown that tetracycline-HCl is a sustentative medication and becomes absorbed and released from tooth structures such as dentin and cementum. The use of tetracycline is also preferred because a very low portion of the general population exhibit allergies or other sensitivities to tetracycline.

In another preferred embodiment, the disinfectant is an antimicrobial compound. It will be apparent to one skilled in the art that the antimicrobial compound should be stable in the acidic solutions of which it forms a part, should be compatible with the other components of the solution, and should retain its effectiveness for at least the time of preparation of the solution and its application and residence time on or in the prepared tooth or bone surface. Examples of such antimicrobial compounds include, but are not limited to, chlorhexidine compounds. Chlorhexidine gluconate is preferred. One example of a suitable chlorhexidine gluconate solution is a commercially available 0.12% solution known as "peridex". Additionally, the use of chlorhexidine gluconate has been found to be especially desirable in patients who exhibit sensitivity or allergy to tetracycline compounds.

It will also be recognized by one skilled in the art that the detergent used should be stable in acidic solution with an antibiotic compound. Additionally preferable is a detergent that reduces surface tension of the solution, thus providing an increased wetting effect and permitting enhanced penetration of the irrigation solution into dentinal tubules and irregular spaces that are otherwise difficult to reach. Furthermore, the detergent should be one suitable for use in situ in dental applications without deleterious effect to the human or animal subject.

In a preferred embodiment, the detergent is a non-ionic surfactant or similar compound, preferably one commonly used in the food and drug industry or approved for use by the Food and Drug Administration. Examples of such compounds include, but are not limited to, mono- and di-glycerides; sucrose esters; sorbitan esters (also known as SPANs), particularly sorbitan monostearate; sorbitols; polysorbates (polyoxyethylene sorbitan esters, also known in industry as TWEENs), particularly polysorbate 20, polysorbate 60, polysorbate 65, and polysorbate 80; stearoly lactylates; lecithin and derivatives; polyglycol fatty acid esters; p-Cymene; quaternary ammonium compounds; sodium alkyl sulfonates; triethanolamine; and alkyl polysaccharides.

In another preferred embodiment, the detergent used is selected from the group of sorbitan esters or polysorbates. One exemplary member of the preferred class is polysorbate 80 (polyoxyethylene sorbitan monooleate).

It will also be apparent to one of skill in the art of dentistry that the acid used should be suitable for dental application. Thus, the acid should be nontoxic in the applicable concentration and amount used in the irrigation process and should also be compatible with the detergent and disinfectant selected as the other components of the solution. Preferred acids must also be capable of dissolving the organic and inorganic components of the smear layer within the chosen exposure time, but without inducing unwanted erosion of the tooth and surrounding surfaces.

In another preferred embodiment, the acid is an organic acid, preferably having pKa values between 1.5 and 5. Further preferred are carboxylic acids or other acids with a polar nature and pKa values between 2 and 5. In a further preferred mode of the present invention, an acid with a pKa value between about 2.75 and 3.75 is used. One exemplary member of the preferred class is citric acid. Citric acid is particularly suitable when tetracycline is chosen as the disinfectant, because citric acid does not diminish or otherwise alter the antibacterial effect of tetracycline.

It will be apparent to one skilled in the art, however, that stronger acids may also be preferred for use in the present invention provided that the time of application of the solution is shortened accordingly. As such, stronger acids including, but not limited to, chloracetic, maleic, saccharic, tartaric, and polyacrylic may be used, having pKa values ranging from about 0.5 to about 3.0. Mixtures may also be used. In some embodiments inorganic acid, specifically phosphoric acid may find utility so long as the essential properties of the solution are maintained.

The disinfectants are present in the solutions of the present invention in weight percentages of from about 1 to about 5 percent of the solution and preferably in amounts of from about 2 to about 4 weight percent, with amounts of about 3 percent being even more preferred, especially when the disinfectant is a tetracycline.

The detergent is preferably present in the solutions of the invention in weight percentages of from about 0.1 to about 1.5 percent of the solution, with amounts of from about 0.25 to about 1.0 percent being more preferred. Amounts by weight of about 0.5 percent are generally most preferred depending upon the detergent, especially when the detergent is a polysorbate.

The acids of the invention are present in the solutions in amounts of from about 0.5 to about 10 percent by weight of the solution, preferably from about 3 to about 6 percent. More preferred are solutions having weight percentages of acid, especially organic acid, of from about 4 to about 5 percent.

In general, the solutions of the invention are aqueous and water comprises the bulk of the balance of the composition. Solutions of the invention may also include other compounds, however, so long as they do not interfere with the essential functions of the principal components, do not cause them to degrade and do not interfere with the convenience and utility thereof. Such additional additives may include colorants, flavorants, stabilizers, and other materials conventionally added to dental or orthopaedic solutions. One particularly useful adjuvant may be chelating agents capable of rendering chelatable materials, especially metals, soluble. Indeed, use of a polyfunctional acid may achieve this goal. It will be recognized by one of skill in the art that regardless of the components or additives in the solution, the resulting solution should be sterile so that the objectives of the invention are achieved. In all cases, such materials are present in effective amounts to accomplish their objectives.

In a preferred embodiment of the current invention, the solution comprises an aqueous solution of 3% doxycycline, 0.5% polysorbate 80, and 4.25% citric acid by weight. While these components have previously been used separately and in high concentrations in efforts to remove the smear layer, the three components as described above have not been combined as in the present invention. Additionally, studies performed in conjunction with the present invention using a solution of 3% doxycycline, 0.5% polysorbate 80, and 4.25% citric acid have shown low levels of cytotoxicity and no mutagenicity when compared to all purpose bleach, which had previously been used to disinfect tooth preparations.

Additional studies performed with a solution of doxycycline, polysorbate 80, and citric acid have shown further superior properties. For example, the solution exhibits lower toxicity than eugenol, 3% $H_2O_2$, $Ca(OH)_2$ paste, peridex, and EDTA, and exhibits greater antimicrobial properties than 5.25% NaOCl, even when applied to infected root canals for brief periods of time, such as 2 and 5 minute intervals of use. It will be apparent to those of skill in the art that a solution such as the one described herein (i.e., one that has improved biocompatibility and is effective in a shorter period of time than previously known treatments) is highly desirable, particularly in the health care fields. Studies have also shown that, unlike other previously known dental irrigants, the solution of the present invention maintains the desired antimicrobial effect at dilutions up to 1:200. In contrast, the bactericidal properties of NaOCl cease to exist at dilutions of about 1:32, and EDTA is ineffective in anything other than an undiluted state. In a further study undertaken to evaluate the antimicrobial properties of the presently described solution, human root canals were infected with whole saliva and then treated with either 5.25% NaOCl or a solution of doxycycline, polysorbate 80, and citric acid. While the NaOCl effectively disinfected only 37 out of 60 teeth, the solution of the present invention disinfected 59 out of 60 teeth. The importance and desirability of such improved antimicrobial properties can be easily appreciated, particularly by those of skill in the art.

The present invention is directed to methods for sterilizing and removing the smear layer on a prepared tooth or canal surface comprising irrigating the surface with a solution comprising disinfectant, detergent, and acid. In preferred modes of the invention, the disinfectant is an antibiotic that is sufficiently stable in an acidic environment. It is further preferred that the antibiotic be a tetracycline compound. In a further preferred embodiment, the tetracycline compound is doxycycline. In other preferred modes of the invention, the detergent is an FDA-approved additive, preferably a polysorbate or sorbitan ester compound. In another preferred mode of the invention, the detergent is polyoxyethylene sorbitan monooleate (polysorbate 80).

In another preferred aspect of the present invention, the acid is an organic acid, preferably having a pKa between 1.5 and 5. In a further preferred embodiment, the organic acid has a pKa between 2 and 4; preferably between 2.75 and 3.75, such as that of citric acid. In a further embodiment, the acid is phosphoric acid.

The methods of the present invention can be used on surfaces of instrumented root canals, sites prepared for periodontic procedures, sites prepared for tooth restoration or reconstruction, and sites prepared for bone restoration or reconstruction. In a preferred mode of the present invention, the prepared tooth surface is irrigated for between 1 minute and 1 hour, preferably between 1 and 30 minutes and more preferably from about 1 to about 10 minutes.

Although the uses described above are exemplary for the present invention, there are other embodiments that may be foreseen by those skilled in the art. The solution of the present invention can also have use in preparation for implants in the animal body. Such foreseeable preparations include use with cochlear, cranial, sternum, other custom implants or functional shapes made for the body. Other embodiments can be used for preparation for insertion of universal plates for orthopedic use, bone screws, rods & pins for orthopedic use (IM nails, femoral rods or plugs, long bone fractures, etc.), tendon anchors, suture anchors and tacks, graft retainers and marrow sampling ports.

For use in connection with removal of smear layer from bony preparations, either in the mouth or upon skeletal bone, a prepared site is irrigated for from 1 minute to one hour, preferably from 1 minute to about 30 minutes, with from about 1 to 10 minutes being preferred. By "irrigation" is meant contacting the site with the solution. It is preferred to provide a flow of such solution over the surfaces of the site, however, this need not be performed continuously. Flow of solution may be accompanied by air entrainment to assist in smear layer removal through action of the ensuing bubbles. Other physical means of assisting with smear layer removal may accompany irrigation and all such are encompassed hereby.

Following irrigation, the site is dried and used for the intended restoration.

It has further been discovered that the solutions of the present invention can be particularly effective when used following an initial rinse comprising NaOCl. In such applications, NaOCl may be used as an irrigant in conjunction with instrumentation of a surface. Following instrumentation and use of the NaOCl rinse, a final rinse of disinfectant/detergent/acid solution may be applied to the surface. This method is believed to have an improved effect on smear layer removal because the initial NaOCl rinse removes some organic materials from the smear layer, while the disinfectant/detergent/acid solution removes inorganic and residual organic materials. When NaOCl is used in conjunction with the solution of the present invention, it is preferred that the concentration of NaOCl be between about 1% and about 6% by weight, and the concentration is most preferably between about 1.3% and about 5.25% by weight. Because testing indicates that there is no significant difference in performance within this concentration range, and high concentrations of NaOCl are known to be more toxic than lower concentrations, it is recommended that NaOCl at the lower end of the given concentration range be used. A method comprising the use of an initial rinse of a solution of 1.3% NaOCl by weight followed by a final rinse of a solution comprising doxycycline, polysorbate 80, and citric acid is particularly desirable.

In a further embodiment, it may be beneficial to take steps to increase the shelf life of the prepared solution. For example, in a preferred embodiment, the prepared solution is dehydrated and then the resulting powder is rehydrated with an appropriate amount of distilled water prior to use. Persons of skill in the art will recognize that there are many ways to effectively dehydrate the solution, for example by dessicating, lyophilizing, spray drying, or by any other method that renders the solution in a shelf-stable powdered form. By this method, the shelf life of the solution is increased significantly. Furthermore, the powdered solution may simply be rehydrated with an appropriate amount of distilled water and then used to irrigate prepared surfaces in accordance with the procedures described above.

EXAMPLES

The invention is illustrated by the following examples, which are not intended to be limiting.

Example 1

Removal of Smear Layer from Root Canal Walls

Extracted maxillary and mandibular human teeth were used for this study. The working lengths of these teeth were between 21-25 millimeters. The teeth were scaled of any calculus and other surface debris (soft tissue and/or alveolar bone) using hand scalers. After preparing conventional access preparations through the incisal or occlusal surfaces of the test teeth, a K-type file (size 10) was used to determine the working length of each tooth by penetrating the apical foramen and pulling back to the clinical apical foramen. A combination of passive step back technique and rotary files (Rivera and Walton 2002) were used to clean and shape the root canals. Each canal was cleaned and shaped using a combination of passive step back and Rotary 0.04 Taper NITI files (Rivera and Walton, 2002). The apex of each tooth was enlarged to size 30 files.

The teeth were randomly assigned to one of the two groups: Group 1: Non-surgical endodontic therapy (NSET) was performed using 5.25% sodium hypochlorite as an irrigant. After complete cleaning and shaping, the canals were irrigated with 1 ml of NaOCl and a barbed broach wrapped with cotton was taken to the canal terminus and left for five minutes to ensure uniform direct contact of the irrigant with the entire canal. Upon removal of the barbed broach, the canal was irrigated with 4 ml of NaOCl and rinsed with 10 ml of distilled water. Group 2: NSET was performed using 1% sodium hypochlorite as root canal irrigant. After complete cleaning and shaping of teeth in this group, the canals were irrigated with 1 ml of a mixture of 3% doxycycline, 0.5% polysorbate 80, and 4.25% citric acid, hereinafter referred to as "ADD" (acid, disinfectant, and detergent) solution, and a barbed broach wrapped with cotton was taken to the canal terminus and left for five minutes to ensure uniform direct contact of the irrigant with the entire canal. Upon removal of the barbed broach, the canal was irrigated with 4 ml of ADD and rinsed with 10 ml of distilled water. After irrigation, the teeth were split in half using a diamond saw and constant water spray. Half of each tooth was placed into a gluteraldehyde solution for 24 h. The fixed specimens were then rinsed twice by a sodium buffered solution (pH 7.2), treated with osmium tetraoxide for one hour, rinsed with ascending concentrations of ethyl alcohol 30%-100%, and then placed in a dessicator for 24 h. Finally, each specimen was mounted on a special button, and coated with 25 µm of gold-palladium (Au—Pd) (Wakabayashi et al., 1995). The presence or absence of smear layer at the coronal, middle, and apical portion of each canal was evaluated. The erosion of dentinal tubules was also assessed at different levels of each canal.

Examinations of the specimens showed presence of smear layer on the entire root canal walls of all teeth prepared in Group 1. In contrast, the walls of canals in Group 2 had no detectable smear layer in any sample. There was a significant difference between the two groups. No erosion was noted in the dentinal tubules at various levels of each canal treated with ADD.

Example 2

Removal of Smear Layer from Coronal Cavity Preparations

Sound third molars were collected and stored in deionized water. Class I preparations were made following conventionally accepted procedures in the occlusal surfaces of the teeth. The teeth were randomly divided into two groups.

Group 1: A solution of 5.25% of NaOCl was left in the cavity for 5 minutes. After this treatment each preparation was rinsed with copious amounts of water to eliminate the residual effect of sodium hypochlorite.

Group 2: ADD solution was left in the cavity for 5 minutes. After this treatment each preparation was rinsed with copious amounts of distilled water to eliminate the residual effect of ADD.

After irrigation, the crowns were split in half using a diamond saw and constant water spray. Half of each sample was placed into a gluteraldehyde solution for 24 h. The fixed specimens were then rinsed twice by a sodium buffered solution (pH 7.2), treated with osmium tetraoxide for one hour, rinsed with ascending concentrations of ethyl alcohol 30%-100%, and then placed in a dessicator for 24 h. Finally, each specimen was mounted on a special button, and coated with 25 µm of gold-palladium (Au—Pd) (Wakabayashi et al., 1995). The presence or absence of smear layer on the walls of each cavity was evaluated. The erosion of dentinal tubules was also assessed.

Examinations of the specimens showed presence of smear layer on the walls of all teeth prepared in Group 1. In contrast, the walls of cavities in all samples in Group 2 had no smear layer and had patent dentinal tubules. There was a significant difference between the two groups.

No erosion was noted in the dentinal tubules of cavities in Group 2 treated with ADD.

Example 3

Removal of Smear Layer from Prepared Crown Preparations

Sound third molars were collected and stored in deionized water. Crown preparations were made following conventionally accepted procedures. The samples were randomly divided into two groups.

Group 1: A cotton pellet saturated with a 5.25% NaOCl solution was left on the crown preparations for 5 minutes. After this treatment each preparation was rinsed with copious amounts of distilled water to eliminate the residual effect of sodium hypochlorite.

Group 2: A cotton pellet saturated with ADD solution was left on the crown preparations for 5 minutes. After this treatment each preparation was rinsed with copious amounts of distilled water to eliminate residual ADD.

After irrigation, the crown preparations were split in half using a diamond saw and constant water spray. Half of each sample was placed into a gluteraldehyde solution for 24 h. The fixed specimens were then rinsed twice by a sodium buffered solution (pH 7.2), treated with osmium tetraoxide for one hour, rinsed with ascending concentrations of ethyl alcohol 30%-100%, and then placed in a dessicator for 24 h. Finally, each specimen was mounted on a special button, and coated with 25 µm of gold-palladium (Au—Pd) (Wakabayashi et al., 1995). The presence or absence of smear layer on the walls of each cavity was evaluated. The erosion of dentinal tubules was also assessed.

Examinations of the specimens showed presence of smear layer on the surface of all crowns prepared in Group 1. In contrast, the surfaces of crowns prepared in Group 2 had no smear layer and had patent dentinal tubules. There was a significant difference between the two groups. No erosion was noted in the dentinal tubules of crown preparations in Group 2.

Example 4

Removal of Smear Layer from Root Surfaces of Teeth

Sound extracted teeth were used in this experiment. The coronal one-third root surfaces of these teeth were curetted following conventionally accepted procedures. The samples were randomly divided into two groups.

Group 1: A cotton pellet saturated with a 5.25% NaOCl solution was left on the surfaces of root preparations for 5 minutes. After this treatment each root surface was rinsed with copious amounts of distilled water to eliminate the residual effect of sodium hypochlorite.

Group 2: A cotton pellet saturated with ADD solution was left on the root surface preparations for 5 minutes. After this treatment each preparation was rinsed with copious amounts of distilled water to eliminate the residual effect of ADD.

After irrigation, the entire tooth was split in half using a diamond saw and constant water spray. Half of each sample was placed into a gluteraldehyde solution for 24 h. The fixed specimens were then rinsed twice by a sodium buffered solution (pH 7.2), treated with osmium tetraoxide for one hour, rinsed with ascending concentrations of ethyl alcohol 30%-100%, and then placed in a dessicator for 24 h. Finally, each specimen was mounted on a special button, and coated with 25 µm of gold-palladium (Au—Pd) (Wakabayashi et al., 1995). The presence or absence of smear layer on the root surfaces was evaluated. The erosion of dentinal tubules was also assessed.

Examinations of the specimens showed presence of smear layer on the surface of all roots prepared in Group 1. In contrast, the surfaces of roots prepared in Group 2 had no smear layer and had patent dentinal tubules. There was a significant difference between the two groups. No erosion was noted in the dentinal tubules of root preparations in Group 2.

Example 5

Removal of Smear Layer from Root End Cavity Preparations

Extracted, human single-rooted teeth were used in this part of the experiment. The clinical crown of each tooth was removed at the cemento-enamel junction using a #701 fissure bur in a high-speed handpiece and water spray.

The working length of each canal was determined by placing and moving a #15 K file apically in the canal until it exited from the apical foramen. After enlarging the apical foramen to a #40 K file, the rest of the canal was cleaned and shaped using a combination of passive step-back technique and rotary instruments (Rivera and Walton, 2002), while a 5.25% NaOCl solution was used as the intracanal irrigant.

The instrumented canals were dried with paper points and obturated with laterally condensed gutta-percha and Roth 811 sealer. The access cavities were closed with Cavit. The roots were then wrapped in moist gauze and stored in a closed glass bottle at room temperature and 100% humidity for one week.

Two coats of nail polish were applied to the external surface of each root. Apical root resections were then performed by removing 3-4 mm of the apex, at a 90° angle to the long axis of the root, with a #701 fissure bur in a high-speed hand piece with water coolant.

Apical cavity preparations were made in each of the roots. A #1 round bur in a high-speed handpiece with water coolant was used to create a small opening into the gutta-percha filling material. The cavities were enlarged and deepened to approximately 3 mm using a #701 fissure bur in high-speed handpiece with water spray. A # 541 med 108/010: HIDI diamond bur in a high speed handpiece with water spray was then used to standardize the preparation to a diameter of 1.5 mm and a depth of 3 mm.

The roots were then randomly divided into two groups. In Group 1, the apical preparations were rinsed 5.25% NaOCl. The solution was left in the cavity for five minutes and then rinsed with 10 ml of distilled water. In Group 2, the preparations were rinsed with 5 ml of ADD. This solution was also left in the root end cavities for five minutes and then rinsed with 5 ml of distilled water. After drying with paper points, the roots were split in halves using a slow speed diamond saw (Labut Agar Scientific, Cambridge, England).

Half of each sample was placed into a gluteraldehyde solution for 24 h. The fixed specimens were then rinsed twice by a sodium buffered solution (pH 7.2), treated with osmium tetraoxide for one hour, rinsed with ascending concentrations of ethyl alcohol 30%-100%, and then placed in a dessicator for 24 h. Finally, each specimen was mounted on a special button, and coated with 25 µm of gold-palladium (Au—Pd) (Wakabayashi et al., 1995). The presence or absence of smear layer on the root end cavity preparations was evaluated. The erosion of dentinal tubules was also assessed.

Examinations of the specimens showed presence of smear layer on the surface of all cavity preparations prepared in Group 1. In contrast, the surfaces of cavities prepared in Group 2 had no smear layer and had patent dentinal tubules. There was a significant difference between the two groups. No erosion was noted in the dentinal tubules of root end cavity preparations in Group 2.

Example 6

Removal of Smear Layer from Prepared Bone Sites

A 0.5 mm dental drill was used to drill cavities in extracted tibia segments of mature male rats. 5 ml of distilled water was used as an irrigant during drilling. The resulting cavities were 0.6 to 1.0 mm in diameter.

Following drilling, each prepared cavity was irrigated with 5 ml of a solution of 3% tetracycline, 0.5% polysorbate 80, and 4.25% citric acid. After irrigation, the solution was left in the bone cavity for 5 minutes. The bones were then split in half using a diamond saw and constant water spray. Half of each bone fragment was then placed in 4% formaldehyde solution for 24 hours. The segments were then dehydrated in serial ethanol concentrations and embedded in polymethylmethacrylate (PMMA). The specimens were then coated with a gold palladium film for SEM examination.

Visual SEM inspection showed substantially complete removal of the smear layer on all samples.

Example 7

Removal of Smear Layer in Conjunction with NaOCl Rinse

Eighty extracted maxillary and mandibular single and multi-rooted human teeth were used for this study. In multi-rooted teeth, the root with the largest canal was included in the study. Teeth with previous root canal treatment were excluded. The teeth were randomly divided into 7 experimental groups of 10 teeth each and two control groups of 5 teeth each. The teeth were grouped according to the type of irrigants and final rinses used during and after instrumentation.

After preparing a conventional access preparation for each tooth, a K-type file (size 10 or 15) was used to determine the working length by penetrating the apical foramen and pulling back to into the clinical apical foramen. The working length of each tooth was between 21 and 25 millimeters. Each canal was instrumented using a combination of passive step back and Rotary 0.04 Taper NITI files (Millefer ProFile, Switzerland). The apical foramen of each tooth was enlarged to a size 30 file. Distilled water, various concentrations of NaOCl (0.65%, 1.3%, 2.6%, and 5.25%), and ADD solution were used as intracanal irrigants. One milliliter of irrigation solution was used to irrigate the root canal between each hand and rotary instrument. A total of 10 mL of irrigant was used in each canal. The irrigants were delivered with a 27-gauge plastic needle (Ultra dent Products South Jordan, Utah, USA) that penetrated to within 1-2 mm from the working length in each canal. Each canal was filled with an irrigant during instrumentation. The instrumentation time for each root canal was approximately 18-20 minutes. To determine the effect of control and experimental solutions as a final rinse on the surface of instrumented root canals, the canals were then treated with 5 mL of one of the following solutions for 2 minutes: sterile distilled water (positive control), 17% EDTA (negative control), 5.25% NaOCl, and ADD solution.

After instrumentation, each canal was initially irrigated with 1 mL of one of the above solutions. After 2 minutes, each canal was irrigated with 4 mL of one of the control or experimental solutions as a final rinse. These irrigants were also delivered with a 27-gauge plastic needle (Ultra dent Products South Jordan, Utah, USA) that penetrated to within 1-2 mm from the working length in each canal. The total exposure time for the final rinse was approximately 2 minutes. The canals were then irrigated with 10 mL of sterile distilled water and dried with paper points. The teeth were then split longitudinally and half of each tooth was placed in a 2% glutaraldehyde solution for 24 hours. The fixed specimens were rinsed 3 times with a sodium cacodylate buffered solution (0.1 M, pH 7.2), incubated in osmium tetraoxide for 1 hour, dehydrated with ascending concentrations of ethyl alcohol (30%-100%), and then placed in a dessicator for at least 24 hours. Each specimen was mounted on an aluminum stub, and coated with 25 μm of gold-palladium and examined under a scanning electron microscope.

The specimens were examined to determine the extent of both removal of smear layer and erosion of the dentinal tubules. The most effective combination at removing smear layer while minimizing erosion was 5.25% NaOCl-ADD (expressed as "initial rinse solution-final rinse solution"), followed by 2.6% NaOCl-ADD, 1.3% NaOCl-ADD, ADD-ADD, distilled water-ADD, 5.25% NaOCl-5.25% NaOCl, and distilled water-distilled water (the least effective combination). A combination of 5.25% NaOCl-17% EDTA was effective for removing smear layer, but resulted in moderate to severe erosion of the dentinal tubules. Statistically, there was no significant difference between the performance of initial rinses of 1.3%, 2.6% and 5.25% NaOCl in combination with a final rinse of ADD.

Example 8

Antibacterial Effect of Varying Dilutions of ADD Solution

Two methods were used to determine the extent of antimicrobial activity of ADD in comparison with NaOCl and EDTA at varying dilutions. In the first test, the zone of inhibition was measured on plates inoculated with *Enterococcus faecalis*. An overnight culture of *E. faecalis* (ATCC 4082) was standardized to 0.11 optical density (O.D.) measured at 570 nm. One hundred microliters of the microorganism was spread onto a trypticase soy agar (TSA) plate with the use of a sterile L-shaped glass rod. One-quarter inch sterile S & S filter paper (Schleicher & Schuell) was placed in each of the four quadrants of the TSA plate. Twenty microliters of sterile saline, 5.25% NaOCl, ADD, or 17% EDTA was added onto the filter papers. Eight replicates were prepared for each of the sample solutions. The plates were incubated overnight at 37° C. for 24 hours and the zones of inhibition were measured in millimeters.

In the second test, the minimum inhibitory concentration (MIC) was measured. *E. faecalis* was cultured overnight and the concentration was adjusted to 0.11 O.D. at 570 nm. The test solutions were serially diluted from 1:2 up to 1:2048 dilutions. One ml of 2× trypticase soy broth (TSB) and the same amount of a test solution were mixed in various tubes. One hundred microliters of the standardized *E. faecalis* was added into each of the test tubes and were incubated overnight at 37° C. The presence or absence of turbidity was determined the following day.

In order to determine whether the test solutions had inhibitory or bactericidal effect, a high concentration of bacteria ($1\times10^8$ c.f.u. of *E. faecalis*) was exposed to 2 ml of undiluted and 1:2 dilution ADD or NaOCl for 2 or 5 minutes. Samples were placed on TSA media to determine viability of any remaining bacteria.

Dilution of the solutions reduced the zones of inhibition for all solutions, albeit at different rates. NaOCl and ADD were both more effective when undiluted than at 1:5 or 1:10 dilution, but both still had some bactericidal effect upon dilution. EDTA, however, demonstrated no bactericidal properties when diluted five- or ten-fold. With respect to the minimum inhibitory concentration tests, EDTA exhibited no antibacterial effects at any dilution level, while NaOCl was effective at dilutions up to 1:32 and ADD was effective at dilutions up to 1:200. Additionally, after both 2 and 5 minutes of exposure at both undiluted and 1:2 dilution levels, ADD resulted in completely negative cultures, while NaOCl did not.

Each of the patents, publications, and other documents mentioned or referred to in this specification is herein incorporated by reference in its entirety. Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A method for removing smear layer from a prepared tooth surface comprising irrigating the surface with a sterile solution comprising about 3% doxycycline by weight of the solution, about 0.5% polysorbate 80 by weight of the solution, and about 4.25% citric acid by weight of the solution.

2. A method for removing smear layer from a prepared tooth comprising the steps of:
   (a) irrigating the surface with a solution of 1.3% NaOCl by weight of the solution; and
   (b) further irrigating the surface for from about 2 to about 5 minutes with a sterile solution comprising about 3% doxycycline by weight of the solution, about 0.5% polysorbate 80 by weight of the solution, and about 4.25% citric acid by weight of the solution.

3. The method of claim 2 wherein the solution of step (b) is diluted up to about 1:200.

4. The method of claim 2 wherein the components of the solution of step (b) are provided in powdered form, further comprising the step of rehydrating the powder with distilled water before irrigation.

* * * * *